United States Patent [19]

Kasai et al.

[11] Patent Number: 4,840,907
[45] Date of Patent: Jun. 20, 1989

[54] PROCESS FOR PRODUCING OPTICALLY ACTIVE DICHLOROPROPANOL USING MICROORGANISM

[75] Inventors: Naoya Kasai, Kishiwada; Hisaharu Shima, Amagasaki; Kazuya Tsujimura, Sakai, all of Japan

[73] Assignee: Osaka Soda Co., Ltd., Osaka, Japan

[21] Appl. No.: 869,711

[22] Filed: Jun. 2, 1986

[30] Foreign Application Priority Data

Jul. 3, 1985 [JP] Japan ................. 60-147065

[51] Int. Cl.⁴ ............ C12R 1/38; C12P 41/00; C12P 7/04
[52] U.S. Cl. .................. 435/253.3; 435/157; 435/280; 435/874
[58] Field of Search ............ 435/155, 243, 253, 280, 435/874–877, 157, 253.3; 568/841

[56] References Cited

U.S. PATENT DOCUMENTS 4,204,044 5/1980 Suhara et al. .................. 435/876 X

FOREIGN PATENT DOCUMENTS 60-176592 9/1985 Japan .................. 435/155

OTHER PUBLICATIONS

Cambou et al., J. Am. Chem. Soc., 106:2687–2692 (1984).
Ellis et al., J. Chem. Soc. Chem. Commun., 1984, 1600–1602.
Iriuchijima et al., Agric. Biol. Chem., 46(6):1593–1597 (1982).
Baldwin et al., J. Org. Chem., 43(25):4876–4878 (1978).
Chemical Abstracts, 98, 104113d, 1983.
Chemical Abstracts, 105, 151578g, 1986.

*Primary Examiner*—Robert J. Warden
*Assistant Examiner*—Randall E. Deck
*Attorney, Agent, or Firm*—Sherman and Shalloway

[57] ABSTRACT

A process for producing optically active dichloropropanol, which comprises cultivating an R-(+)-2,3-dichloro-1-propanol-assimilating strain belonging to the genus Pseudomonas in a culture medium containing racemate 2,3-dichloro-1-propanol, and recovering optical isomer S-(-)-2,3-dichloro-1-propanol from the culture broth, and a process for producing optically active epichlorohydrin, which comprises reacting the optical isomer S-(-)-2,3-dichloro-1-propanol obtained by the aforesaid process with an alkali.

7 Claims, No Drawings

PROCESS FOR PRODUCING OPTICALLY ACTIVE DICHLOROPROPANOL USING MICROORGANISM

This invention relates to a novel process for producing an optical isomer, S-(−)-2,3-dichloro-1-propanol, known as a synthesis intermediate for optically active epichlorohydrin, medicines and agricultural chemicals selectively from a known racemate, 2,3-dichloro-1-propanol, in one step with industrial advantage.

More specifically, this invention relates to a process for producing optically active dichloropropanol, which comprises cultivating an R-(+)-2,3-dichloro-1-propanol-assimilating strain belonging to the genus Pseudomonas in a culture medium containing racemate 2,3-dichloro-1-propanol, and recovering optical isomer S-(−)-2,3-dichloro-1-propanol from the culture broth.

This invention also pertains to a process for producing optionally active epichlorohydrin, which comprises reacting the optical isomer S-(−)-2,3-dichloro-1-propanol obtained by the above process with an alkali, particularly an alkali metal hydroxide selected from sodium hydroxide and potassium hydroxide.

This invention further relates to a pure culture of an R-(+)-2,3-dichloro-1-propanol-assimilating strain belonging to the genus Pseudomonas named Pseudomonas OS K-29, particularly FERM BP-994, which is suitable for use in the above process.

Synthesis of optically active epichlorohydrin is known and described, for example, in J. Org. Chem., vol. 43, page 4876, 1978 (Baldwin et al.), and J. Chem. Soc., Chem. Commun., page 1600, 1984 (Ellis et al.). The conventional synthesis methods, however, have the disadvantage of requiring highly sophisticated synthetic techniques, and no method has been now which can synthesize optically active epichlorohydrin having a high optical purity by a simple procedure.

On the other hand, a method of producing an optically active ester or alcohol has been known which comprises asymmetrically hydrolyzing an ester represented by the following formula

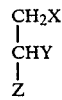

where X represents an acyloxy group, Y represents a halogen atom or an acyloxy group or taken together with Z, an oxygen atom forming an oxirane ring, and Z represents a halomethyl or acyloxymethyl group when Y is a halogen atom, a halomethyl or aryl group when Y is an acyloxy group, and a methylene group forming an oxirane ring together with Y when Y is an oxygen atom, with a lipase or microorganism having the ability to induce asymmetric hydrolysis of the ester (Japanese Laid-Open Patent Publication No. 48888/1981 laid-open on May 2, 1981). The co-inventors of the above-cited Japanese Laid-Open Patent Publication No. 48888/1981 reported asymmetric hydrolysis of (±)-1-acetoxy-2,3-dichlororopane with enzymes and micoorganisms in Agric. Biol. Chem., 46 (6), 1593–1597, 1982.

These literature references, however, totally fail to refer to the asymmetric hydrolysis of racemate 2,3-dichloro-1-propanol, which is not in an ester form but in an alchohol form, to its optical isomer with the use of a microorganism. Furthermore, none of the microorganisms specifically described in Table 3 of the above-cited Japanese Laid-Open Patent Publication No. 4888/1981 are microorganisms of the genus Pseudomonas.

The present inventors have made extensive investigations in order to develop a process for producing an optical isomer S-(−)-2,3-dichloro-1-propanol from racemate 2,3-dichloro-1-propanol using microorganisms.

Consequently, they have succeeded in isolating a microorganism having the ability to assimilate R-(+)-2,3-dichloro-1-propanol from the soil. It has been found that this novel strain is an R-(+)-2,3-dichloro-1-propanol-assimilating strain belonging to the genus Pseudomonas, and that by cultivating this microorganism strain in a culture medium containing racemate 2,3-dichloro-1-propanol, R-(+)-2,3-dichloro-1-propanol can be selectively assimilated by the strain, and the optical isomer S-(−)-2,3-dichloro-1-propanol can be easily recovered from the culture broth.

Investigations of the present inventors have shown that it is necessary to contact the strain with the racemate 2,3-dichloro-1-propanol in the culture medium, and if an enzyme is extracted from the above strain and contacted with the racemate 2,3-dichloro-1-propanol, the optical isomer S-(−)-2,3-dichloro-1-propanol cannot formed.

It has also been found by the present inventors that if an ester, such as an acetate, of the racemate 2,3-dichloro-1-propanol is used instead of the racemate 2,3-dichloro-1-propanol, the optical isomer can neither be formed.

It is an object of this invention therefore to provide a novel process for producing an optically active dichloropropanol by which the optical isomer S-(−)-2,3-dichloro-1-propanol can be obtained selectively in one step from the racemate 2,3-dichloro-1-propanol utilizing a microorganism.

The above and other objects of this invention along with its advantages will become apparent from the following description.

The microbiological characteristics of the strain OS-K-29 (FERM BP 994) are listed below.

A. Morphological characteristics
   (1) Shape and size of cells:
       rods; single cell, straight; 0.4–0.6 × 1.2–1.8 μm
   (2) Pleomorphisms of cells: none
   (3) Mobility: +, polar flagella
   (4) Spores: none
   (5) Gram stain: negative
   (6) Acid fastness: none B. Cultural characteristics
   (1) Plate culture of nutrient agar (for 3 days at 30° C.)
      (a) Speed of colony growth: ordinary, about 3–4 mm in diameter
      (b) Shape of colonies: circular
      (c) Shape of colony surface: smooth
      (d) Raised condition of colonies: convex
      (e) Periphery of colonies: entire
      (f) Contents of colonies: homogeneous
      (g) Color of colonies: milky white
      (h) Transparency of colonies: semitransparent
      (i) Gloss of colonies: dull
      (j) Formation of soluble pigments: none
   (2) Slant culture of nutrient agar (for 3 days at 30° C.)
      (a) Growth: good, filiform
      (b) Shape of colonies: smooth
      (c) Raised condition of colonies in section: flat
      (d) Gloss of colonies: dull
      (e) Shape of colony surface: smooth
      (f) Transparency of colonies: semitransparent
      (g) Color of colonies: milky white
   (3) Nutrient liquid culture (for 3 days at 30° C.)

-continued (a) Growth: pellicular
    (b) Turbidity: slightly turbid
    (c) Gas production: none
    (d) Coloration of the medium: none
  (4) Stab culture of nutrient gelatin
    No liquefaction of gelatin
  (5) Litmus milk
    No coagulation: litmus color to pale blue to colorless
C. Physiological characteristics
    (Symbols: +, positive; −, negative)
  1. Reduction of nitrate: +
  2. MR test: −
  3. VP test: −
  4. Indole production: −
  5. Formation of hydrogen sulfide: −
  6. Hydrolysis of starch: −
  7. Denitrification: −
  8. Utilization of citric acid: +
  9. Utilization of inorganic nitrogen sources: +
 10. Formation of pigments: fluorescent pigment formed on Sellers differential agar
 11. Urease: +
 12. Oxidase: +
 13. Catalase: +
 14. Growth range: pH 5.5–9.0; temperature 20–37° C.
 15. Aerobiosis: aerobic
 16. O-F test (Hugh Leifson method): O
 17. Formation of acids and gases from sugars

| Sugar | Acid | Gas |
|---|---|---|
| (1) D-glucose | + | − |
| (2) D-galactose | + | − |
| (3) sucrose | + | − |
| (4) trehalose | + | − |
| (5) starch | − | − |

The above characteristics have been analyzed with reference to Bergey's Manual of Determinative Bacteriology, 8th edition, and the present strain has been identified as a novel strain belonging to the genus Pseudomonas. The R-(+)-2,3-dichloro-1-propanol-assimilating strain belonging to the genus Pseudomonas isolated by the present inventors and having the above microbiological characteristics has been named Pseudomonas OS-K-29. A pure culture of this stain has been deposited in Fermentation Research Institute, Agency of Industrial Science and Technology, Japan under deposit number FERM BP-994 in accordance with Budapest Treaty on the international recognition of the deposit of microorganisms for the purposes of patent procedure.

According to the process of this invention, the R-(+)-2,3-dichloro-1-propanol-assimilating strain belonging to the genus Pseudomonas is cultivated in a culture medium containing racemate 2,3-dichloro-1-propanol. The culture medium may contain other carbon sources in addition to the 2,3-dichloro-1-propanol, and further nitrogen sources and minerals. In one preferred embodiment, the culture medium may further contain one or more other carbon sources, one or more nitrogen sources and one or more minerals in addition to the racemate 2,3-dichloro-1-propanol. The amount of the racemate 2,3-dichloro-1-propanol in the culture medium can be properly selected, and is, for example, not more than about 0.2% by volume, preferably about 0.001 to about 0.2% by volume. Examples of such other carbon sources carbohydrates such as glucose, sucrose and glycerol, organic acids such as citric acid, maleic acid and malic acid, and salts of such organic acids. Examples of the nitrogen sources include inorganic nitrogen sources such as ammonium sulfate, ammonium chloride, ammonium nitrate and ammonium phosphate, and organic nitrogen sources such as urea, peptone, casein, yeast extracts and meat extracts. Examples of the minerals includes phosphates, magnesium salts, potassium salts, manganese salts, iron salts, zinc salts and copper salts.

In the practice of the process of this invention, there can be used well grown microbial cells obtained by cultivating the R-(+)-2,3-dichloro-1-propanol-assimilating strain belonging to the genus Pseudomonas in a synthetic medium contaning racemate 2,3-dichloro-1-propanol as a carbon source, inorganic nitrogen (e.g., an ammonium salt or a nitrate) as a nitrogen source and inorganic salts, or in an ordinary nutrient medium containing organic nutrient sources and inorganic nutrient sources such as a bouillon medium or a sugar-containing bouillon medium. The use of such well grown cells is preferred.

Preferably, the cultivation of the R-(+)-2,3-dichloro-1-propanol-assimilating strain of the genus Pseudomonas in the aforesaid medium in the process of this invention is carried out under aerobic conditions. Aerobic cultivating means such as shaking culture and aeration agitation culture may be used for this purpose. The cultivation may be carried out at a temperature of, for example, about 20° to about 40° C., preferably about 25° to about 37° C., and a pH of, for example, about 6 to about 9, preferably about 6.5 to about 7.5. The cultivation time may properly be selected, and is, for example, about 2 to about 10 days.

After the cultivation, the optical isomer S-(−)-2,3-dichloro-1-propanol may be recovered from the culture broth. This can be effected, for example, by separating the culture broth into microbial cells and the supernatant by means of a suitable solid-liquid separating procedure such as centrifugal separation, and separating S-(−)-2,3-dichloro-1-propanol in the supernatant by treatment with a charcoal column, extraction with ether, distillation under reduced pressure, etc.

In the practice of the process of this invention, the R-(+)-2,3-dichloro-1-propanol-assimilating strain belonging to the genus Pseudomonas may be used in an immobilized form fixed to an inert substrate. Means of fixation are known per se and can be utilized in this invention. For example, living cells of the strain may be fixed by using such a substrate as acrylamide, K-carrageenan, agar, gelatin or sodium alginate. After fixation, the cells may be crushed into a suitable size and shape, and used in the process of this invention. The use of immobilized cells has the advantage that the operation of separating the supernatant and the cells from the culture broth after the cultivation becomes easy, and the immobilized cells may be repeatedly used.

According to this invention, there is also provided a process for producing optically active epichlorohydrin, which comprises reacting the optical isomer S-(−)-2,3-dichloro-1-propanol obtained as above with an alkali. This process can be carried out by contacting S-(−)-2,3-dichloro-1-propanol with the alkali in an aqueous medium. The reaction temperature may, for example, be about 0° C. to room temperature (for example, about 30° C.). Examples of the alkali are alkali metal hydroxides and alkali metal alcoholates. Specific examples of the alkali are sodium hydroxide, potassium hydroxide, lithium hydroxide, sodium methylate and sodium ethylate.

The following examples illustrate the present invention in more detail.

In the following examples, all percentages are by weight unless otherwise specified, and β-DCH stands for 2,3-dichloro-1-propanol.

EXAMPLE 1

One platinum loopful of a slant agar culture of Pseudomonas OS-K-29 (FERM BP-994) was inoculated in each of ten 500 ml Sakaguchi flasks each containing 100 ml of a culture medium having the following composition which contained racemate β-DCH as a sole carbon source.

Racemate β-DCH: 0.2% by volume
Ammonium sulfate: 0.05% by weight
Ammonium nitrate: 0.05% by weight
Dipotassium hydrogen phosphate: 0.1% by weight
Disodium phosphate: 0.1% by weight
Monosodium phosphate: 0.2% by weight
Magnesium sulfate: 0.05% by weight
Iron sulfate, copper sulfate and manganese sulfate: traces
pH: 6.5

The strain was then cultivated under shaking at 30° C. for 5 days. The culture broth was then added to a 25-liter jar fermentor containing 20 liters of a culture medium of the above composition, and cultivated with aeration and agitation for 3 days under the following conditions.

Temperature: 30° C.
pH: 6.5 at the start of cultivation
Amount of air passed: 20 liters/min.
Agitation: 300 rpm After the cultivation, the culture broth was taken out and subjected to a centrifugal separator to separate it into microbial cells and the supernatant. The supernatant containing β-DCH was charged onto a column (5 cm in diameter and 90 cm in length) packed with charcoal, and the column was eluted with 3 liters of acetone to obtain 1.5 liters of acetone solution containing β-DCH. Acetone was evaporated from this solution until the amount of the solution became 200 ml. Then, 500 ml of ether was added to extract β-DCH. The ethereal layer was dried over magnesium sulfate. The ether was then evaporated, and the residue was distilled to give 6.6 g of an oily substance having a boiling point at 84° C./24 mmHg. The resulting substance was identified by the following method.

(1) Identification by Gas Chromatography

When the substance was compared with commercial β-DCH using PEG-20MP as a column carrier (60–80 mesh), the retention times were quite the same. The purity of the substance was more than 98.2%.

(2) Identification by Infrared Absorption Spectroscopy

The absorption pattern of the substance was quite the same as that of commercial β-DCH.

The above results led to the determination that the substance obtained in this example was β-DCH.

By the following methods, this substance was determined to be S-(−)-β-DCH.

(1) Measurement of Specific Rotation

The specific rotations of commercial β-DCH and the present substance were as follows:

Commercial β-DCH
$[\alpha]_D^{20} = 0.0$ (c = 1, acetone)
$[\alpha]_D^{20} = 0.0$ (c = 1, dichloromethane)
Present substance
$[\alpha]_D^{20} = +3.5$, (c = 1, acetone)
$[\alpha]_D^{20} = -12.0$, (c = 1, dichloromethane)

(2) Preparation of R-(+)-α-methoxy-α-trifluoromethylphenyl acetate and analysis by high-performance liquid chromatography R-(+)-α-methoxy-α-trifluoromethylphenyl acetate chloride was reacted with each of the present substance and commercial β-DCH to prepare its ester derivative. The derivatives were analyzed by liquid chromatography under the following conditions, and the following results were obtained.

Analysis Conditions

Column carrier: ZORBAXODS, 4.6 mm×25 cm (made by Du Pont)
Eluent: Methanol/water=65:35 (V/V)
Amount eluted: 1 ml/min.
Method of detection: absorbance at 260 nm

Results of Analysis

Commercial β-DCH: Two peaks having the same area were given at a retention time of 50.5 minutes and 52.0 minutes respectively.

Present substance: A peak was given only at a retention time of 50.5 minutes, and no peak was given at a retention time of 52.0 minutes.

(3) Preparation of Dichloropropyl-N-Phenyl-Carbamate and Its Specific Rotation One gram of each of commercial β-DCH and the present substance and 0.9 g of phenyl isocyanate were added to 30 ml of dry acetone and 0.3 ml of triethylamine. The mixture was heated under reflux for about 3 hours to prepare dichloropropyl-N-phenylcarbamate, and its specific rotation was measured.

Commercial β-DCH
$[\alpha]_D^{25} = 0.0$, (c = 1, methanol)
Present substance
$[\alpha]_D^{25} = -16.4$, (c = 1, methanol)

The above results led to the determination that the present substance is S-(−)-β-DCH and its optical purity was more than 99% e.e.

EXAMPLE 2

Five 500 ml Sakaguchi flasks containing 100 ml of a culture medium containing 1.0% of meat extract, 1.0% of polypeptone and 0.5% of glucose and having a pH of 7 were sterilized with heated steam in a customary manner. One platinum loopful of a slant agar culture of Pseudomonas OS-K-29 (FERM BP-994) was inoculated into each of the flasks, and cultivated at 30° C. for 48 hours with reciprocal shaking at 200 rpm.

A 30-liter jar fermentor was charged with 20 liters of a culture medium having the above composition, and sterilized with pressurized steam. The microbial cells grown in each of the flasks were aseptically inoculated in the jar fermentor and cultivated for 48 hours under the following conditions.

Temperature: 30° C.
pH: 7.0 at the start of cultivation
Amount of air passed: 20 liters/min.
Agitation: 300 rpm After the cultivation, the culture broth was subjected to a centrifugal separator and separated into microbial cells and the supernatant. The supernatant was discarded. The remaining microbial cells were washed three to four times with 50 mM phosphate buffer (pH 6.5) to obtain washed cells. The washed cells were then suspended in 20 liters of the culture medium containing racemate β-DCH shown in Example 1, and maintained under the following conditions.

Temperature: 30° C.
Amount of air passed: 20 liters/min.
Agitation: 300 rpm
pH: 5.5 (maintained at this pH by adding 20 g of calcium carbonate)

The above cultivation with aeration and agitation was carried out for 48 hours after the washed cells were added to the culture medium. The culture broth was again separate into microbial cells and the supernatant by a centrifugal separator. The separation of β-DCH from the supernatant was carried out in the same way as in Example 1 to give 7.0 g of β-DCH. The β-DCH obtained was found to be S-(−)-β-DCH having an optical purity of more than 99% e.e.

Twenty liters of a culture medium containing 1.0% of meat extract, 2.5% of glucose and 1.0% of polypeptone was put into a 30-liter jar fermentor, and sterilized by heating in a customary manner. Then, Pseudomonas OS-K-29 (FERM BP-994) was inoculated into the fermentor, and cultivated for 48 hours under the following conditions.

Temperature: 30° C.
pH: 7.0 at the start of cultivation
Amount of air passed: 20 liters/min.
Agitation: 300 rpm After the cultivation, the culture broth was separated into microbial cells and the supernatant by means of a centrifugal separator to give 540 g of living cells. Then, the living cells were suspended in a synthetic medium having the following composition to a volume of 10 liters, and then fixed with acrylamide in a customary manner. The immobilized cells were pulverized by a mixer to small fragments each side measuring 0.5 to 1 mm, and well washed with the synthetic medium.

| Composition of the synthetic medium | |
|---|---|
| Ammonium sulfate | 0.05% |
| Ammonium nitrate | 0.05% |
| Dipotassium hydrogen phosphate | 0.1% |
| Monosodium phosphate | 0.2% |
| Disodium phosphate | 0.1% |
| Magnesium sulfate | 0.05% |
| Iron sulfate, copper sulfate and manganese sulfate | traces |
| pH | 6.8 (initial) |

The immobilized cells were put into a 100-liter jar fermentor and the amount of them and the synthetic medium was adjusted to 80 liters. Furthermore, 160 ml of racemate β-DCH and 150 g of calcium carbonate were added, and the cultivation system was agitated under the following conditions.

Temperature: 30° C.
Amount of air passed: 40 liters/min.
Agitation: 300 rpm

Seventy-two hours after the initiation of the reaction, the supernatant was separated from the immobilized cells by filtration. The purification of β-DCH from the supernatant was carried out in the same way as in Example 1 by charging the supernatant onto a charcoal column. Subsequent ether extraction and distillation under reduced pressure gave 88 g of β-DCH. This substance was identified in the same way as in Example 1 by comparison with commercial β-DCH. It was found that this substance was S-(−)-β-DCH having an optical purity of at least 99% e.e. Then, 30.8 g of S-(−)-β-DCH, 200 ml of a 1.4N aqueous solution of sodium hydroxide and 200 ml of ether were mixed in a 1000 ml flask and vigorously agitated at room temperature for 80 minutes. The ethereal layer was separated, and dried over magnesium sulfate. Ether was evaporated, and the residue was distilled to obtain 9.2 g of epichlorohydrin. The purity of epichlorohydrin measured by gas chromatography was more than 99.4%. Its specific rotation was as follows:

$$[\alpha]_D^{25} = -34.2° \ (c=3.4, \text{methanol})$$

The resulting epichlorohydrin was R-(−)-epichlorohydrin having an optical purity of more than 99% e.e.

EXAMPLE 4

Forty grams of optically active S-(−)-2,3-dichloro-1-propanol ($[\alpha]_D^{25} = -10.4$, c=1.36, methylene chloride; optical purity more than 99% e.e.) was put into a 300 ml Erlenmeyer flask, and while it was vigorously agitated by a magnetic stirrer, 258 ml of a 1.5N aqueous solution of sodium hydroxide was added dropwise over the course of 5 minutes. After the addition, the agitation was continued for another 20 minutes. The reaction mixture was then well mixed with 150 ml of ether in a separating funnel. The ethereal layer was separated and dried over magnesium sulfate. Subsequently, epichlorohydrin contained in the ethereal layer was collected by distillation as 16.74 g (yield 72.0%) of a fraction having a boiling point of 115° to 117° C. The resulting epichlorohydrin had a gas-chromatographic purity of more than 98.5% and an optical purity of more than 99% e.e. ($[\alpha]_D^{25} = -34.0$, c=1.2, methanol). The distillation residue was found to be the unreacted 2,3-dichloro-1-propanol (4.3 g). It did not at all undergone racemization, and could be re-used.

What is claimed is:

1. A process for producing optically active dichloropropanol, which comprises cultivating the R-(+)-2,3-dichloro-1-propanol-assimilating strain Pseudomonas OS-K-29 as deposited with the Fermentation Research Institute, Agency of Industrial Science and Technology, Japan, under Deposit No. FERM BP-994 in a culture medium containing racemate 2,3-dichloro-1-propanol and recovering optical isomer S-(−)-2,3-dichloro-1-propanol from the culture broth.

2. The process of claim 1 wherein the strain is in an immobilized form.

3. The process of claim 1 wherein the cultivation is carried out under aerobic conditions.

4. The process of claim 1 wherein the cultivation is carried out at a temperature of about 20° to about 40° C.

5. The process of claim 1 wherein the cultivation is carried out at a pH of about 6 to about 9.

6. The process of claim 1 wherein the culture medium further contains at least one carbon source, at least one nitrogen source and at least one mineral.

7. A pure culture of an R-(+)-2,3-dichloro-1-propanol-assimilating strain Pseudomonas OS-K-29 as deposited with the Fermentation Research Institute, Agency of Industrial Science and Technology, Japan, under Deposit No. FERM BP-994.

* * * * *